United States Patent
Fosaaen

(10) Patent No.: US 10,067,034 B2
(45) Date of Patent: Sep. 4, 2018

(54) WIDEBAND OXYGEN SENSING

(71) Applicant: Kerdea Technologies, Inc., Greenville, NC (US)

(72) Inventor: Ken Ervin Fosaaen, Winterville, NC (US)

(73) Assignee: KERDEA TECHNOLOGIES, INC., Greenville, NC (US)

(*) Notice: Subject to any disclaimer, the term of this patent is extended or adjusted under 35 U.S.C. 154(b) by 0 days.

(21) Appl. No.: 15/450,643

(22) Filed: Mar. 6, 2017

(65) Prior Publication Data

US 2017/0176289 A1 Jun. 22, 2017

Related U.S. Application Data

(62) Division of application No. 14/073,222, filed on Nov. 6, 2013, now Pat. No. 9,625,352.

(Continued)

(51) Int. Cl.
*G01K 7/42* (2006.01)
*G01M 15/10* (2006.01)
(Continued)

(52) U.S. Cl.
CPC .......... *G01M 15/104* (2013.01); *F01N 11/007* (2013.01); *F02D 41/1445* (2013.01); *F02D 41/1446* (2013.01); *F02D 41/1455* (2013.01); *F02D 41/1458* (2013.01); *F02D 41/2416* (2013.01); *G01N 27/4065* (2013.01);
(Continued)

(58) Field of Classification Search
None
See application file for complete search history.

(56) References Cited

U.S. PATENT DOCUMENTS 3,915,135 A 10/1975 Kushida et al.
4,245,314 A 1/1981 Henrich et al.
(Continued)

FOREIGN PATENT DOCUMENTS

CN 101208450 A 6/2008
CN 101825032 A 9/2010
(Continued)

OTHER PUBLICATIONS

JPS61155746—tranlation.*
(Continued)

*Primary Examiner* — Lisa Caputo
*Assistant Examiner* — Nasir U Ahmed
(74) *Attorney, Agent, or Firm* — Coats & Bennet, PLLC

(57) ABSTRACT

An oxygen sensor that has both an n-type oxygen sensing portion comprising an n-type semiconductor layer and a p-type oxygen sensing portion comprising an p-type semiconductor layer. The n-type sensing portion and the p-type sensing portion share the common electrode. The n-type semiconductor layer and the p-type semiconductor layer attach directly to the common electrode, but are not in physical contact with each other such that a lateral gap exists between the n-type semiconductor layer and the p-type semiconductor layer. The air:fuel ratio for a combustion process may be determined, using the same oxygen sensor, across a range of air:fuel values in both the rich and lean regions; as such, the oxygen sensor may act as a wideband oxygen sensor.

15 Claims, 9 Drawing Sheets

Related U.S. Application Data

(60) Provisional application No. 61/725,209, filed on Nov. 12, 2012.

(51) Int. Cl.
 *F02D 41/14* (2006.01)
 *F02D 41/24* (2006.01)
 *G01N 27/406* (2006.01)
 *F01N 11/00* (2006.01)
 *G01N 33/00* (2006.01)

(52) U.S. Cl.
 CPC ..... *G01N 33/0016* (2013.01); *G01N 33/0036* (2013.01); *H05K 999/99* (2013.01); *F01N 2560/025* (2013.01); *F01N 2560/20* (2013.01); *F02D 41/2438* (2013.01)

(56) References Cited

U.S. PATENT DOCUMENTS

| | | |
|---|---|---|
| 4,263,652 A | 4/1981 | Henrich |
| 4,276,600 A | 6/1981 | Hartford et al. |
| 4,322,968 A | 4/1982 | Takami et al. |
| 4,462,890 A | 7/1984 | Touda et al. |
| 4,500,412 A | 2/1985 | Takahashi et al. |
| 4,535,316 A | 8/1985 | Wertheimer et al. |
| 4,660,407 A | 4/1987 | Takami |
| 4,744,344 A | 5/1988 | Morozumi |
| 5,895,591 A | 4/1999 | Kojima |
| 5,980,728 A | 11/1999 | Farber et al. |
| 6,227,033 B1 | 5/2001 | Kainz |
| 6,256,981 B1 | 7/2001 | Sullivan et al. |
| 6,746,584 B1 | 6/2004 | Wang et al. |
| 7,769,534 B1 | 8/2010 | Xu et al. |
| 7,954,365 B2 | 6/2011 | White et al. |
| 8,086,392 B2 | 12/2011 | Anilovich et al. |
| 2004/0060550 A1 | 4/2004 | Wu et al. |
| 2008/0248288 A1 | 10/2008 | Boardman |
| 2011/0051775 A1 | 3/2011 | Ivanov et al. |
| 2011/0168557 A1 | 7/2011 | Park et al. |
| 2011/0186446 A1 | 8/2011 | Fosaaen |

FOREIGN PATENT DOCUMENTS

| | | |
|---|---|---|
| EP | 0056752 A1 | 7/1982 |
| EP | 0553452 A2 | 8/1993 |
| JP | S61155746 A | 7/1986 |
| JP | 0743342 A | 2/1995 |
| JP | 4171803 B2 | 10/2008 |
| JP | 4607163 B2 | 1/2011 |
| WO | 20110093975 A3 | 8/2011 |

OTHER PUBLICATIONS

Analog Devices, Inc., "Basic Linear Design", Chapter 3: Sensors, Jan. 1, 2007, pp. 1-102, Retrieved on Nov. 18, 2014, retrieved from internet: http://www.analog.com/library/analogdialogue/archives/43-09/EDCh 3 sensors.pdf, XP055153616.

Ramamoorthy, ER., et al., "Oxygen sensors: Materials, methods, designs and applications", Chemical Sensors, Journal of Materials Science, Nov. 1, 2003, pp. 4271-4282, vol. 38, Issue 21.

\* cited by examiner

WIDEBAND OXYGEN SENSING

This application is a divisional of U.S. patent application Ser. No. 14/073,222, filed 6 Nov. 2013, and claims benefit of U.S. Provisional Application No. 61/725,209, filed 12 Nov. 2012, the disclosures of both of which are incorporated by reference herein in their entirety.

BACKGROUND

This application is related to oxygen sensors, methods of using oxygen sensors, and related systems for use with combustion processes, for example in internal combustion engines.

As known by those of skill in the art, the air:fuel ratio in combustion processes, particularly in internal combustion engines, is typically represented by lambda ($\lambda$), with $\lambda$ defined as is the actual air:fuel ratio divided by the air:fuel ratio at the exact stoichiometric mixture. Thus, in mathematical terms $\lambda = \text{air:fuel}_{actual}/\text{air:fuel}_{stoichiometric}$. Values less than 1.0 are fuel-rich (rich), values greater than 1.0 are fuel-lean (lean). For many internal combustion engines, maximum power is achieved around $\lambda=0.86$, and maximum fuel economy is achieved around $\lambda=1.45$-$1.55$. As can be appreciated, engine management systems typically focus heavily on controlling $\lambda$. As such, most large internal combustion engines have oxygen sensors to sense exhaust gas oxygen levels, with the data from the oxygen sensor used by the engine management systems for various engine management functions. For smaller internal combustion engines, such as those used in motorcycles, all-terrain vehicles, recreational marine applications, and unmanned air vehicles, the size constraints of the engines presents difficulties in identifying suitable oxygen sensors.

Fortunately, small resistive-based oxygen sensors are known, see, for example, U.S. Patent Application Publication 2011/0186446. Such oxygen sensors find a particular application in engine management control for small internal combustion engines. In addition, such sensors are useful for individual cylinder control in multi-cylinder engines and hybrid engines for automotive and off-road applications.

The 2011/0186446 oxygen sensor may be considered as a switching oxygen sensor with some unique properties. Such sensors have a drastic change (orders of magnitude) in the resistance of the sensor element when transitioning across the stoichiometric boundary in air:fuel ratio of Lambda ($\lambda$)=1.00. For example, for the n-type semiconductor version of the 2011/0186446 sensor, above this crossover point (in the lean region with $\lambda>1.00$), the sensor's resistance is very high and not significantly responsive to changes in the oxygen content in the gasses to which it is exposed; however, below this crossover point (in the rich region with $\lambda<1.00$) the resistance is significantly lower and has a positive relationship with oxygen content. Conversely, for the p-type semiconductor version of the 2011/0186446 sensor, the resistance is very high in the rich region, but is lower and has a positive relationship with oxygen content in the lean region.

While the 2011/0186446 sensors are useful for many situations, such as those described in the 2011/0186446 publication, there remains a need for alternative oxygen sensor arrangements, and for alternative methods of oxygen sensing and controlling combustion processes based on the sensed oxygen level(s), and related systems.

SUMMARY

The present invention provides a method of determining an air:fuel ratio of a combustion process, and/or related devices and/or systems.

A method according to one or more embodiments includes supplying a constant total sensing current to an oxygen sensing portion of an oxygen sensor, with the oxygen sensing portion exposed to exhaust gases from the combustion process. The oxygen sensor has an n-type sensing circuit and a p-type sensing circuit that share a common electrode. The sensing current is a sum of a first current in the n-type sensing circuit and a second current in the p-type sensing circuit. The first current in the n-type sensing circuit is determined. The second current in the p-type sensing circuit is determined. A temperature value representative of a temperature of the oxygen sensor is determined. Then, a first value representative of the air:fuel ratio of the combustion process is determined based on the current in the n-type sensing circuit, the current in the p-type sensing circuit, and the temperature value.

The first value may be determined based on a ratio of a log of the first current to a log of the second current, and the temperature value.

The determining the temperature value may comprise sensing a heater resistance of a heater portion of the oxygen sensor. The sensing the heater resistance may comprise sensing a current through, and an applied voltage of, a heater circuit that includes the heater portion.

The oxygen sensor may comprise a heater portion and a temperature sensor distinct from the heater portion, and the determining the temperature value may comprise determining the temperature value based on information from the temperature sensor.

The combustion process may be a combustion process of an engine, which may be multi-cylinder engine. The engine may be capable of operating in both a) a rich mode where air and fuel are supplied to a combustion chamber of the engine such that there is less air than a stoichiometric ratio; and b) a lean mode where air and fuel are supplied to the combustion chamber such that there more air than the stoichiometric ratio. The determining the first value may comprise determining the first value while the engine is operating in one of the rich mode or the lean mode. The method may further comprise, after operating in the one of the rich or the lean mode, determining, based on information from the oxygen sensor, a second value representative of the air:fuel ratio, while the engine is operating in the other of the rich mode and the lean mode.

The method may further include controlling the combustion process based on the first value, such as by adjusting a fuel metering rate.

A wideband oxygen sensor according to one or more embodiments, includes a) an n-type oxygen sensing portion comprising an n-type semiconductor layer; and b) a p-type oxygen sensing portion comprising an p-type semiconductor layer. The n-type oxygen sensing portion and the p-type oxygen sensing portion are electrically connected to a constant current source through a shared common electrode of the oxygen sensor. The n-type semiconductor layer and the p-type semiconductor layer are disposed in spaced relation to each other and both attach directly onto the common electrode. The wideband oxygen sensor may optionally and advantageously further include a heater portion disposed in spaced relation to the n-type oxygen sensing portion and the p-type oxygen sensing portion.

A wideband oxygen sensor, according to one or more embodiments includes a) a dielectric substrate; b) a first common electrode affixed to the substrate and having first and second combs, each having a plurality of fingers; c) a first sensing electrode affixed to the substrate and disposed on a first lateral side of the first electrode in spaced relation thereto; d) a second sensing electrode affixed to the substrate and disposed on a second lateral side of the first electrode in spaced relation thereto; e) an n-type semiconducting material disposed so as to interconnect the first comb and the first sensing electrode; f) a p-type semiconducting material disposed in spaced relation to the n-type semiconducting materials and disposed so as to interconnect the second comb and the second sensing electrode. The wideband oxygen sensor may optionally and advantageously further include a heater portion affixed to the substrate in spaced relation to the first common electrode and electrically insulated from the n type semiconducting material and the p-type semiconducting material.

The oxygen sensor may further comprise a first porous dielectric protective layer covering the n-type semiconducting material, and a second porous dielectric protective layer covering the p-type semiconducting material. The first and second porous dielectric protective layers may be formed by different portions of a continuous layer.

The oxygen sensor may be such that the first common electrode comprises a first terminal; the first sensing electrode comprises a second terminal; the second sensing electrode comprises a third terminal. If present, the heater portion may comprise a fourth terminal. The first terminal may be operatively connected to the heater portion.

The dielectric substrate may have first and second oppositely facing surfaces. The heater portion may be disposed on the first surface of the substrate, with the first common electrode and both the first and second sensing electrodes are disposed closer to the second surface of the substrate than to the heater portion.

The oxygen sensor may be configured such that the first common electrode is disposed on the substrate; the first sensing electrode is disposed on the substrate; the second sensing electrode is disposed on the substrate; and the heater portion is affixed to the substrate in spaced relation to the electrodes.

The heater circuit may comprise tungsten, platinum, palladium, other precious metals, ceramic (such as silicon nitride Si3N4), or other materials known in the art.

The oxygen sensor may further comprise control circuits operatively connected to the first common electrode, the first sensing electrode, and the second sensing electrode, with the control circuits comprising: a) a constant current source; b) a first pair of resistors connected in series between the second terminal and the constant current source; c) a second pair of resistors connected in series between the third terminal and the constant current source. The oxygen sensor may comprise an n-type sensing circuit and a p-type sensing circuit. The n-type sensing circuit may comprise the first sensing electrode, the n-type semiconductor layer, the first common electrode, the constant current source, and the first pair of resistors. The p-type sensing circuit may comprise the second sensing electrode, the p type semiconductor layer, the first common electrode, the constant current source, and the second pair of resistors.

A wideband oxygen sensor according to one or more embodiments includes a dielectric substrate; a first common electrode, first and second sensing electrodes, and first and second semiconductor bridges. The first common electrode is affixed to the substrate and has first and second combs, each comb having a plurality of fingers. The first sensing electrode is affixed to the substrate and disposed on a first lateral side of the first electrode in spaced relation thereto. The second sensing electrode is affixed to the substrate and disposed on a second lateral side of the first electrode in spaced relation thereto. The first semiconductor bridge comprises an n-type semiconducting material and is disposed so as to interconnect the first comb and the first sensing electrode. The first semiconductor bridge is attached directly to the first common electrode. The second semiconductor bridge comprises a p-type semiconducting material and is disposed in spaced relation to the n-type semiconducting material and disposed so as to interconnect the second comb and the second sensing electrode. The second semiconductor bridge is attached directly to the first common electrode and not in physical contact with the first semiconductor bridge. The first and second semiconductor bridges are separated from each other by a lateral gap.

The wideband oxygen sensor of may also include a first porous dielectric protective layer covering the n-type semiconducting material, and a second porous dielectric protective layer covering the p-type semiconducting material. The first porous dielectric layer may comprise one or more catalytic precious metals and cerium oxide.

The wideband oxygen sensor may include a heater portion affixed to the substrate in spaced relation to the first common electrode and electrically insulated from the n-type semiconducting material and the p-type semiconducting material. The heater portion may comprise platinum.

The dielectric substrate may have first and second oppositely facing surfaces, with the heater portion disposed on the first surface of the substrate, while the first common electrode and both the first and second sensing electrodes are disposed closer to the second surface of the substrate than to the heater portion.

The wideband oxygen sensor may be configured such that the first common electrode is disposed on the substrate; the first sensing electrode is disposed on the substrate; the second sensing electrode is disposed on the substrate; and the heater portion is affixed to the substrate in spaced relation to the electrodes.

The wideband oxygen sensor may be configured such that the first common electrode comprises a first terminal; the first sensing electrode comprises a second terminal; the second sensing electrode comprises a third terminal; and the heater portion comprises a fourth terminal. The first terminal may be operatively connected to the heater portion.

A wideband oxygen sensor according to one or more embodiments includes a dielectric substrate; a first common electrode affixed to the substrate; an n-type oxygen sensing portion comprising an n-type semiconductor layer; and a p-type oxygen sensing portion comprising an p-type semiconductor layer. The n-type sensing portion and the p-type sensing portion share the common electrode. The n-type semiconductor layer and the p-type semiconductor layer attach directly to the common electrode, but are not in physical contact with each other such that a lateral gap exists between the n type semiconductor layer and the p-type semiconductor layer.

The wideband oxygen sensor may have a first porous dielectric protective layer covering the n-type semiconducting material, and a second porous dielectric protective layer covering the p-type semiconducting material.

The wideband oxygen sensor may have a heater portion affixed to the substrate in spaced relation to the first common electrode and electrically insulated from the n-type oxygen sensing portion and the p-type oxygen sensing portion. The heater portion may comprise platinum.

The dielectric substrate may have first and second oppositely facing surfaces, with the heater portion is disposed on the first surface of the substrate, and the first common electrode and both the n-type oxygen sensing portion and the p-type oxygen sensing portion are disposed closer to the second surface of the substrate than to the heater portion.

A wideband oxygen sensor system according to one or more embodiments includes a wideband oxygen sensor, connecting circuits, an n-type sensing circuit, and a p type sensing circuit. The wideband oxygen sensor may comprise a dielectric substrate; a first common electrode affixed to the substrate; an n-type oxygen sensing portion comprising an n-type semiconductor layer; a p-type oxygen sensing portion comprising an p-type semiconductor layer. The n-type sensing portion and the p-type sensing portion share the common electrode. The n-type semiconductor layer and the p-type semiconductor layer attach directly to the common electrode, but are not in physical contact with each other such that a lateral gap exists between the n type semiconductor layer and the p-type semiconductor layer. The connecting circuits operatively connect to the first common electrode, the n-type semiconductor layer, and the p type semiconductor layer. The connecting circuits include a constant current source; a first pair of resistors connected in series between the n-type semiconductor layer and the constant current source; and a second pair of resistors connected in series between the p type semiconductor layer and the constant current source. The n-type sensing circuit comprises the n-type sensing portion, the constant current source, and the first pair of resistors. The p-type sensing circuit comprises the p-type sensing portion, the constant current source, and the second pair of resistors.

The various aspects discussed above may be used alone or in any combination. The various apparatus disclosed herein may operate according to any combination of various method disclosed herein, and vice versa. Further, the present invention is not limited to the above features and advantages. Indeed, those skilled in the art will recognize additional features and advantages upon reading the following detailed description, and upon viewing the accompanying drawings.

DETAILED DESCRIPTION

In one or more embodiments, the present application is directed to a method of determining an air:fuel ratio based on information from an oxygen sensor exposed to exhaust gases of a combustion process, and related systems. A constant current is supplied to an oxygen sensor that has both an n-type sensing circuit and a p-type sensing circuit that share a common electrode. A first current in the n-type sensing circuit is determined, and a second current in the p-type sensing circuit is determined. In addition, a temperature value representative of a temperature of the oxygen sensor is determined. Then, a first value representative of the air:fuel ratio is determined based on the determined currents and the temperature value. The combustion process may then be controlled based on the first value representative of the air:fuel ratio. The air:fuel ratio may be determined, using the same oxygen sensor, across a range of air:fuel values in both the rich and lean regions; as such, the oxygen sensor may be referred to as a "wideband" oxygen sensor.

For simplicity, the discussion below may generally be in the context of an oxygen sensor for a small displacement gasoline powered internal combustion engine, but it should be understood that the oxygen sensor(s) disclosed herein may be used in other internal combustion engine applications, such a hydrogen powered engines, other hydrocarbon powered engines, diesel engines, Homogeneous Charge Compression Ignition (HCCI) engines, and Reactivity Controlled Compression Ignition (RCCI) engines. Further, the disclosed method(s) may be used with other combustion processes, such as, for example, those found in furnaces and water heaters.

Figure 1:
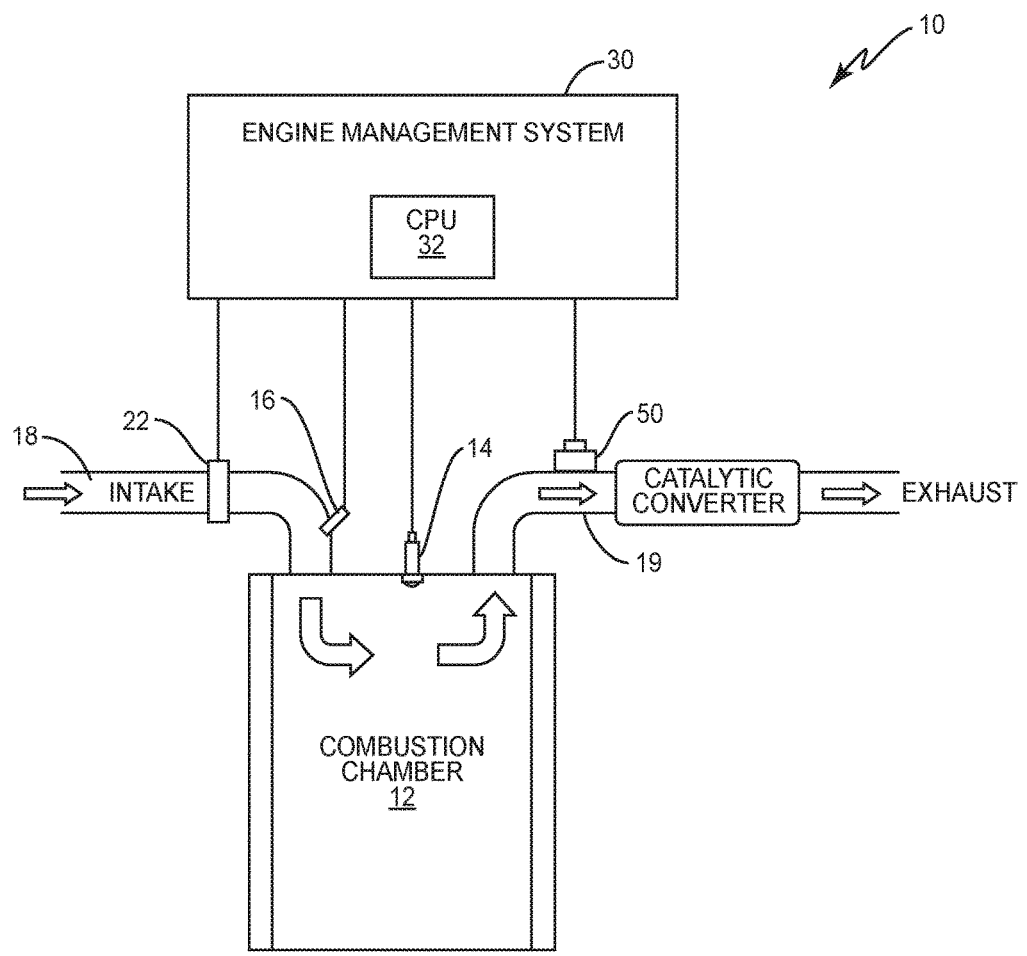
FIG. 1 shows schematic representation of an engine, having an oxygen sensor of the present invention and/or where the method of the one or more embodiments of the present invention may be implemented.

FIG. 1 shows a schematic of an internal combustion engine 10, which may be of any type (e.g., piston, rotary, nutating disk, etc.). The engine 10 includes at least one combustion chamber 12 with associated piston, valves, etc. (note shown), an intake manifold 18, an exhaust manifold 19, and an engine management system 30. The intake manifold 18 supplies air to the combustion chamber 12. An mass airflow sensor 22 advantageously with associated temperature sensor is disposed in the intake 18 manifold so that the incoming air conditions may be monitored and/or controlled. A controllable fuel metering system such as a throttle body and fuel injector 16 supplies fuel to the combustion chamber under control of the engine management system 30. For spark ignition engines, a spark ignition device 14, e.g., spark plug, operates under the control of the engine management system 30 to ignite the air and fuel mixture in the combustion chamber 12 at the desired time in the cycle for proper combustion. An oxygen sensor 50 is disposed in the exhaust plenum 19 to sense the amount of oxygen in the exhaust gases, so that the proper air:fuel ratio may be properly metered and maintained. The engine management system 30 includes one or more processing circuits 32 (collectively "controller") that control the fuel supply, ignition timing, and other engine parameters based on the input from the various sensors and the programming of the processing circuits 32. For example, the engine management system 30 uses the oxygen sensor 50, as described below, to help control the engine 10 so that the engine 10 operates at the desired air:fuel ratio. Other than the particulars of the oxygen sensor 50 and the operation of the processing circuit(s) 32 described in greater detail below, the configuration and operations of the engine 10 are well known to those of skill in the art, and are not discussed further herein in the interests of clarity. As can be appreciated, the engine 10 is able to operate in a rich mode or region where λ<1.00, in a lean mode or region where λ<1.00, and at a stoichiometric point S where λ=1.00.

Figure 2:
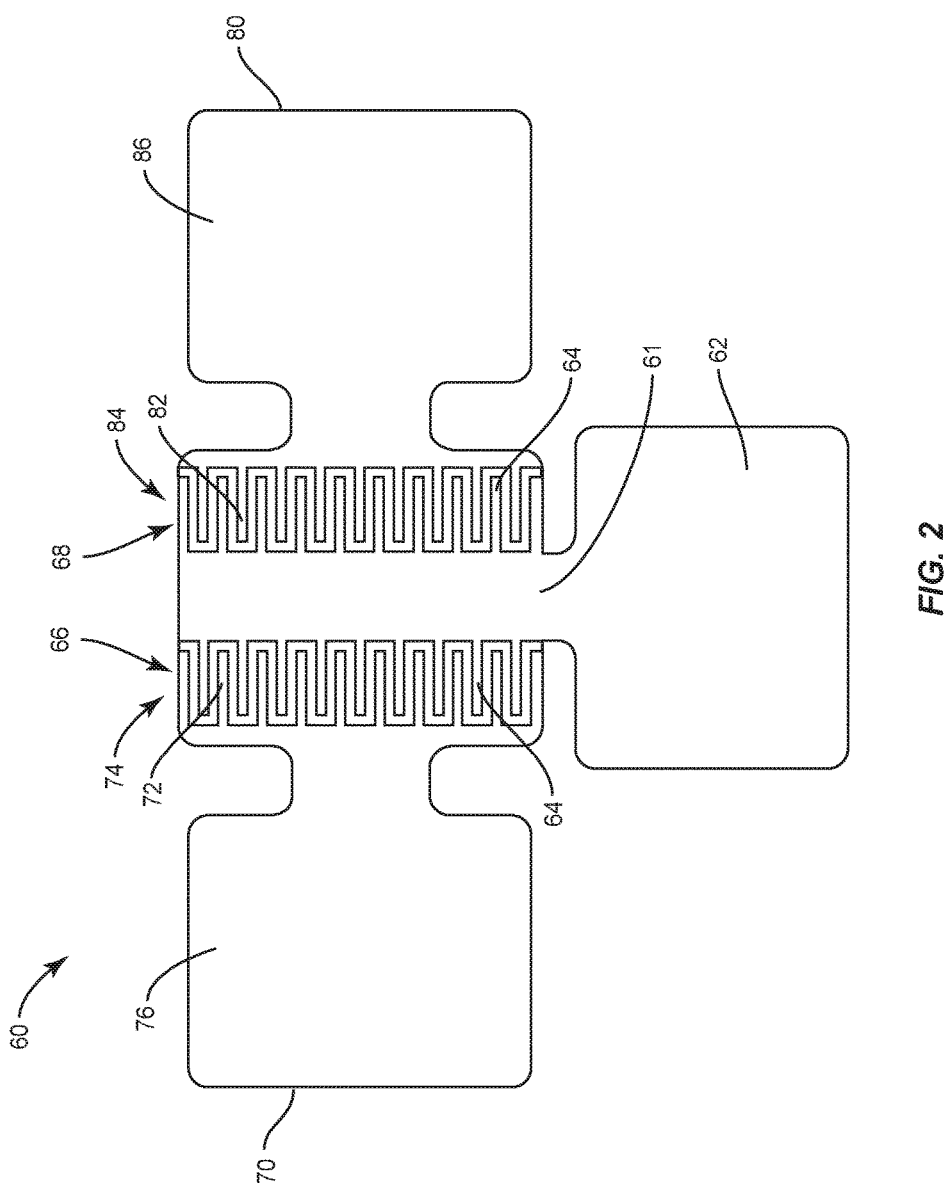
FIG. 2 shows a schematic representation of the substrate and oxygen sensing electrodes of one embodiment of an oxygen sensor.
Figure 3:
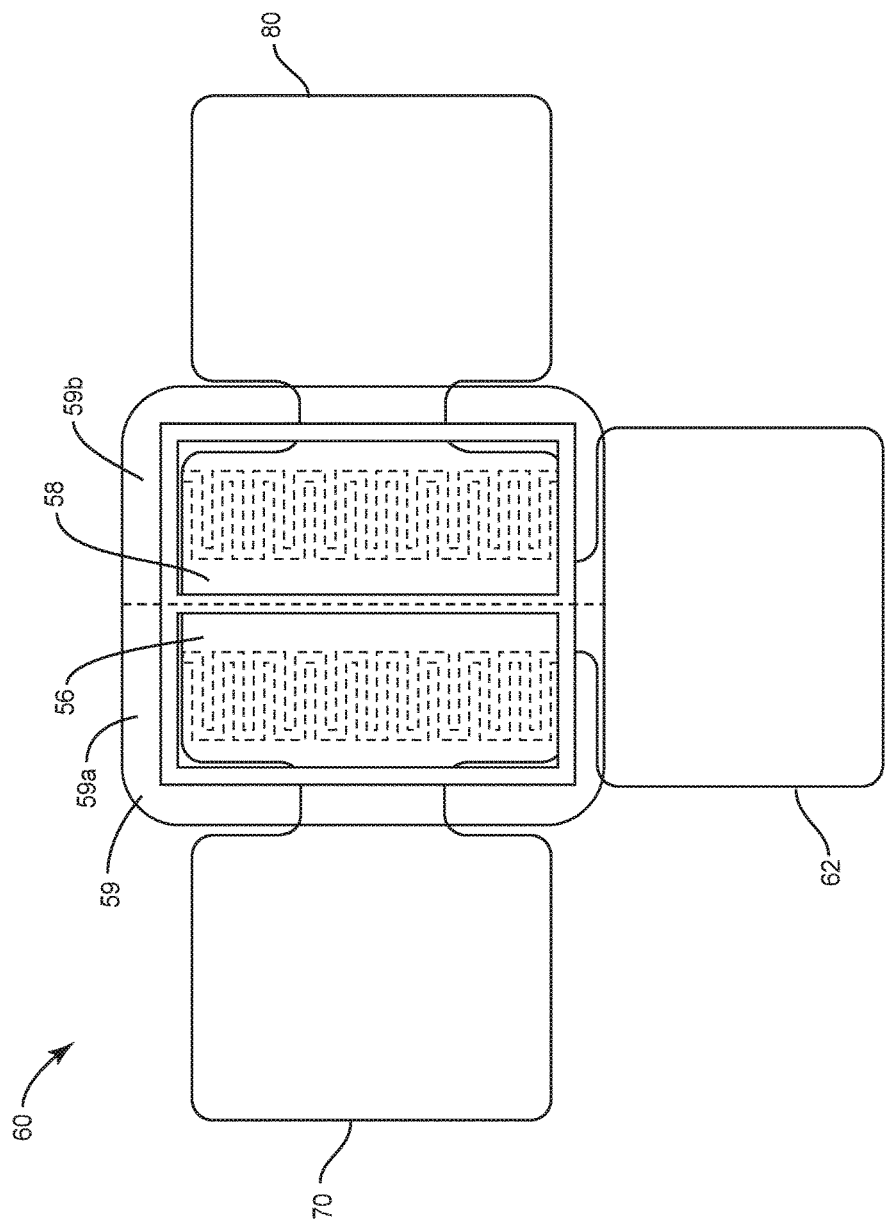
FIG. 3 shows the apparatus of FIG. 2 with the addition of n-type semiconductor layer and a p-type semiconductor layer, and a protective layer.
Figure 4:
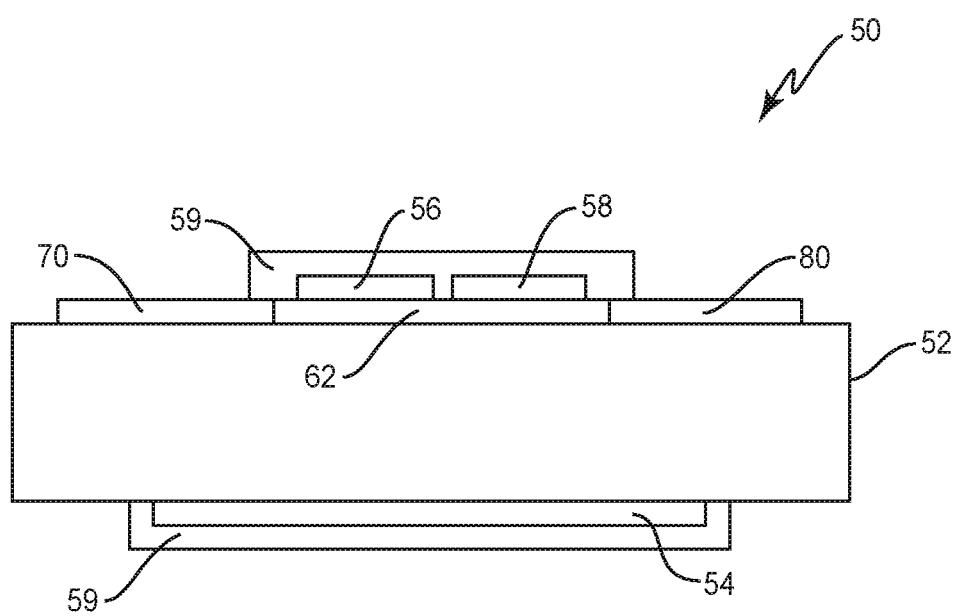
FIG. 4 shows a side view of the apparatus of FIG. 3.

The oxygen sensor 50 is advantageously a resistive-based oxygen sensor. With reference to FIGS. 2-4, the oxygen sensor 50 includes an oxygen sensing portion 60 and optionally a resistance-based heater portion 54. The oxygen sensing portion 60 may advantageously comprise a common electrode 62, a first sensing electrode 70, and a second sensing electrode 80, all disposed on one side of a dielectric substrate 52 which may be a fired ceramic dielectric substrate. The common electrode 62 includes a central area 61 and two sets of fingers 64, each set including a plurality of fingers, that form respective combs 66,68. The combs 66,68 advantageously extend in opposite lateral directions from the central area 61. The first sensing electrode 70 is disposed on one lateral side of the common electrode 62 in spaced relation thereto. The first sensing electrode 70 includes a set of a plurality of fingers 72 that form a comb 74, and a terminal area 76. The comb 74 of the first sensing electrode 70 is advantageously intermeshed with comb 66 of the common electrode 62, with the respective fingers 64,72 being spaced from each other so that there is not direct contact between the two electrodes 62,70. Likewise, the second sensing electrode 80 is disposed on the opposite lateral side of the common electrode 62 from the first sensing electrode 70, and in spaced relation to the common electrode 62. The second sensing electrode 80 includes a plurality of fingers 82 that form a comb 84. The comb 84 of the second sensing electrode 80 is advantageously intermeshed with comb 68 of the common electrode 62, with the respective fingers 64,82 being spaced from each other so that there is not direct contact between the two electrodes 62,80. Further, there is no direct contact between the first and second sensing electrodes 70,80. Note that the electrodes 70,80 may be formed of any suitable material, such as platinum. Note that the length and spacing of the fingers 64,72,82 of combs 66,68,74,84, and their particular materials, including the semiconducting and catalytic materials, may be adjusted as desired for the particular operating conditions for the sensor 50. Note further that the fingers 64,72,82 of electrodes 62,70,80 need not be the same dimensions and that electrodes 70,80 need not be spaced the same from the common electrode 62.

An n-type metal oxide semiconductor layer 56 is placed over combs 66,74 so that the layer 56 forms a semiconductor bridge between the first sensing electrode 70 and the common electrode 62. Likewise a p-type metal oxide semiconductor layer 58 is placed over combs 68,84 so that the layer 58 forms a semiconductor bridge between the second sensing electrode 80 and the common electrode 62. Note that layer 56 and layer 58 should be isolated from each other (no contact). The layers 56,58 are advantageously sintered to the their respective electrodes to ensure good physical and electrical contact. Relevant to the discussion below, it should be understood that an n-type semiconductor has a resistance that is significantly lower and has a positive relationship with oxygen content when exposed to exhaust gases from a combustion process operating in the rich region, while the resistance is relatively high and may be uncorrelated to the oxygen content in the lean region. Conversely, a p-type semiconductor has a resistance that is significantly lower and has a positive relationship with oxygen content when exposed to exhaust gases from a combustion process operating in the lean region, while the resistance is relatively high and may be uncorrelated to the oxygen content in the rich region.

A porous dielectric protective coating layer 59 may be placed over the semiconductor layers 56,58, and neighboring portions of the electrodes. This coating layer 59 may be on continuous coating layer over both semiconductor layers 56,58, with respective first and second portions, or the first portion 59a and second portion 59b may be distinct from each other. This coating layer 59 may include catalytic precious metal(s), such as platinum, and/or palladium, and/or rhodium, as well as oxygen storage components such as cerium oxide or other suitable material as may be necessary to achieve the desired functional characteristics of the oxygen sensing portion 60. These catalytic materials may be an initial part of the composition of the protective layer 59, or added as to impregnate the protective layer 59 in a subsequent operation.

The optional heater portion 54 is advantageously disposed on an opposite side of the dielectric substrate 52 from the oxygen sensing portion 60. See FIG. 4. In other embodiments, the heater portion 54 may be disposed on the same side of the dielectric substrate 52 as the oxygen sensing portion 60, provided the two portions are electrically isolated (other than through ground). In still other embodiments, the heater portion 54 is omitted. The heater portion 54 may take any suitable form and may be formed of any suitable material such as tungsten, platinum, palladium, other precious metals, ceramic (such as silicon nitride $Si_3N_4$), or other materials known in the art. Advantageously, the heater portion 54 is connected to ground and to a voltage source, such as a twelve volt voltage source VS1. The heater portion 54 may also have a suitable protective and/or electrically insulating layer, as desired.

The oxygen sensor 50 may have suitable connections for power and other signals. For example, in some embodiments, the oxygen sensor 50 has four contact pads or leads 55, 69, 79, 89 for making suitable connections. Lead 55 is electrically connected to the heater portion 54, and functions as a power (+) lead for the heater portion 54. Lead 69 is electrically connected to the common electrode 62, and acts as a ground (−) lead. Lead 79 is electrically connected to the first sensing electrode 70, and acts as the input to first sensing electrode 70. Lead 89 is electrically connected to the second sensing electrode 80, and acts as the input to second sensing electrode 80. Lead 69 may also function as a ground lead for heater portion 54, or there may be an additional lead (not shown) for a separate ground lead for heater portion 54.

Figure 5:
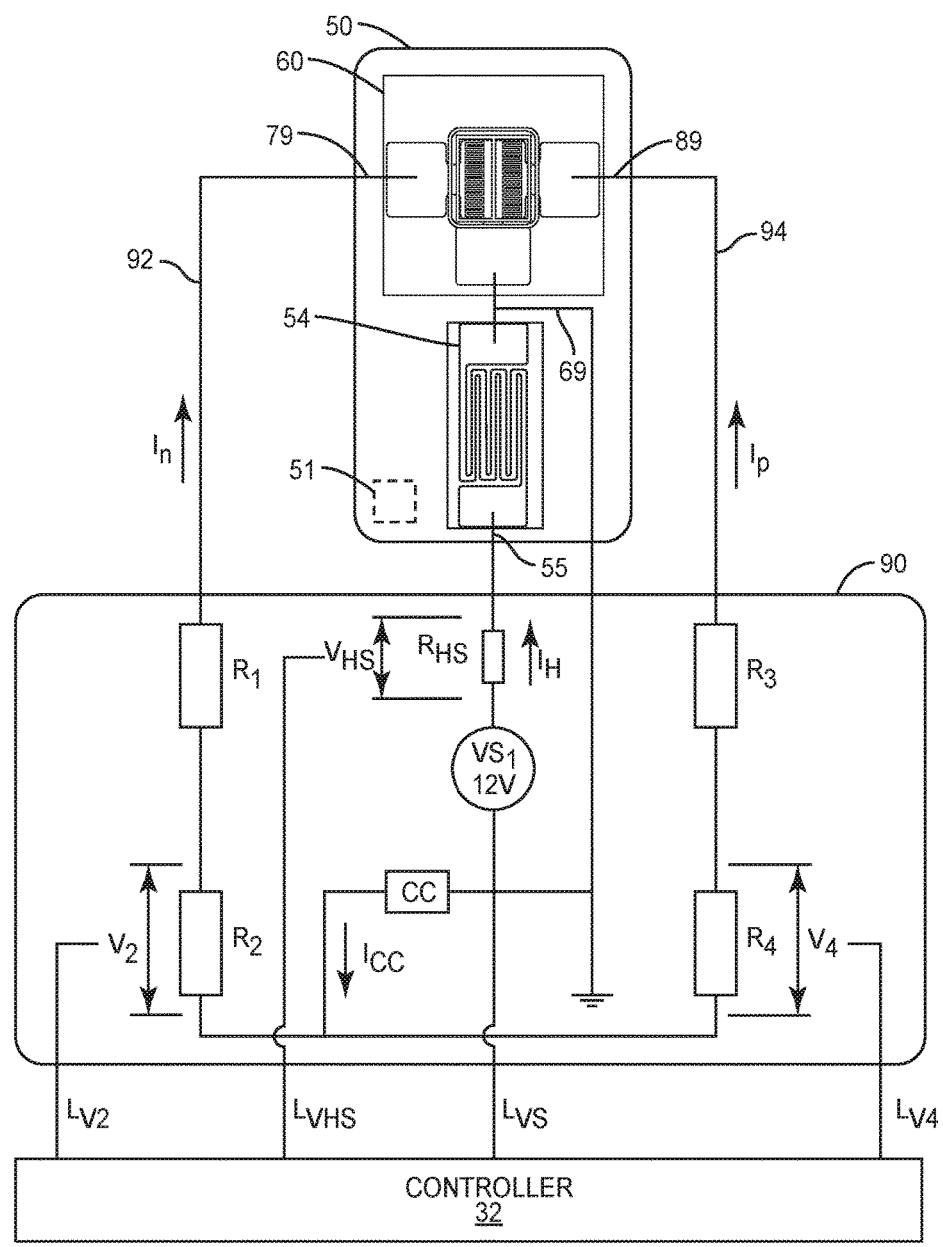
FIG. 5 shows a simplified schematic of the oxygen sensor of FIG. 3 connected to a controller via a connecting circuit.

The oxygen sensor 50 is connected to the controller 32 so that the sensed oxygen level data from the sensor 50 is supplied to the controller 32. In order to facilitate this, the oxygen sensor 50 is, as shown in FIG. 5, connected to the controller 32 via a connecting circuit 90. Note that the connecting circuit 90 may be integrated into an oxygen sensor assembly, integrated into the controller 32, be a separate component or components between the oxygen sensor 50 and the controller 32, or dispersed in any suitable manner. The connecting circuit 90 includes voltage source $VS_1$, which for purposes of this illustrative embodiment will be assumed to be a twelve volt voltage source. Voltage source $VS_1$ connects to one side of heater portion 54 via shunt resistor $R_{HS}$. Suitable leads disposed on either side of shunt resistor $R_{HS}$ allow the voltage drop $V_{HS}$ across shunt resistor $R_{HS}$ to be measured. Note that the line $L_{VHS}$ for $V_{HS}$, as with other voltage drop signals herein, is illustrated and discussed as being a single line merely for the sake of simplicity. The opposing end of heater portion 54 connects to ground.

The connecting circuit 90 also includes a constant current source CC, which will be assumed to be powered using a nominal voltage of five volts or any other suitable power source that is available. The constant current source CC connects to the first sensing electrode 70 via resistors $R_1$ and $R_2$. The voltage drop $V_2$ across resistor $R_2$ is measured and provided by line $L_{V2}$. The n-type sensing circuit 92 is completed to ground via first sensing electrode 70, semiconductor layer 56, and common electrode 62. The constant current source CC connects to the second sensing electrode 80 via resistors $R_3$ and $R_4$. The voltage drop $V_4$ across resistor $R_4$ is measured and provided by line $L_{V4}$. The p-type sensing circuit 94 is completed to ground via second sensing electrode 80, semiconductor layer 58, and common electrode 62. Note that in alternate embodiments, resistor $R_1$ and/or resistor $R_3$ may be omitted from their respective circuits, or additional resistors may be added to their respective circuits.

The connecting circuit 90 provides voltage drop $V_2$ to the controller 32 via line $L_{V2}$, voltage drop $V_{HS}$ to controller 32 via line $L_{VHS}$, the actual voltage $V_S$ of voltage source $VS_1$ to controller 32 via line $L_{VS}$, and voltage drop $V_4$ to the controller 32 via line $L_{V4}$. The information provided by these lines allows the controller 32 to determine the oxygen level sensed by oxygen sensing portion 60, and thus the air:fuel ratio of the combustion process, as explained further below.

The controller 32 may determine the air:fuel ratio based on the current $I_n$ flowing through the n-type sensing circuit 92, the current $I_p$ flowing through the p-type sensing circuit 94, and a value representative of the temperature of the oxygen sensor 50.

The temperature of the oxygen sensor 50 may be determined based on the resistance of the heater portion 54. For example, the current $I_H$ in the heater portion 54 may be calculated as the voltage drop $V_{HS}$ across the shunt resistor $R_{HS}$, divided by the resistance of the shunt resistor $R_{HS}$, or $I_H = V_{HS}/R_{HS}$. Then, the resistance $R_H$ of the heater portion 54 may be calculated based on the voltage drop across the heater portion 54 divided by the current $I_H$ through the heater portion 54. Thus, $R_H$ may be calculated as $R_H = (V_S - V_{HS})/I_H$. Then, using $R_H$, temperature T may be calculated using a suitable formula, for example $T = (M \times R_H) + B$, where the slope M and the constant B are dependent on the heater portion 54 design. As can be appreciated, M and B can be determined in a calibration process, and the relevant values stored in memory of the engine management system 30 for use by the controller 32.

The present invention takes into account that the resistance response of the oxygen sensing portion 60 is temperature dependent. For example, the resistance of the n-type sensing circuit 92 at a given fixed air:fuel ratio in the rich region decreases with increasing temperature, even when the temperature is clearly high enough for a good response. Likewise, the resistance of the p-type sensing circuit 94 at a given fixed air:fuel ratio in the lean region decreases with increasing temperature, even when the temperature is clearly high enough for a good response. The decrease in resistance for a given voltage leads to an increase in current.

The current $I_n$ in the n-type sensing circuit 92 may be calculated as $I_n = V_2/R_2$, with $R_2$ being value known to the controller 32. The current $I_p$ in the p-type sensing circuit 94 may be calculated as $I_p = V_4/R_4$, with $R_4$ being a value known to the controller 32. Note that the total current ICC from constant current source CC is by definition $I_n$ plus $I_p$. With knowledge of both $I_n$ and $I_p$, the controller 32 may determine the air:fuel ratio as a function of $I_n$ and $I_p$, with the value of the air:fuel ratio varying in dependence on both $I_n$ and $I_p$. Thus, the magnitude of the value of the air:fuel varies in dependence on all of $I_n$, $I_p$, and temperature T of the oxygen sensor 50, as described further below.

Figure 6:
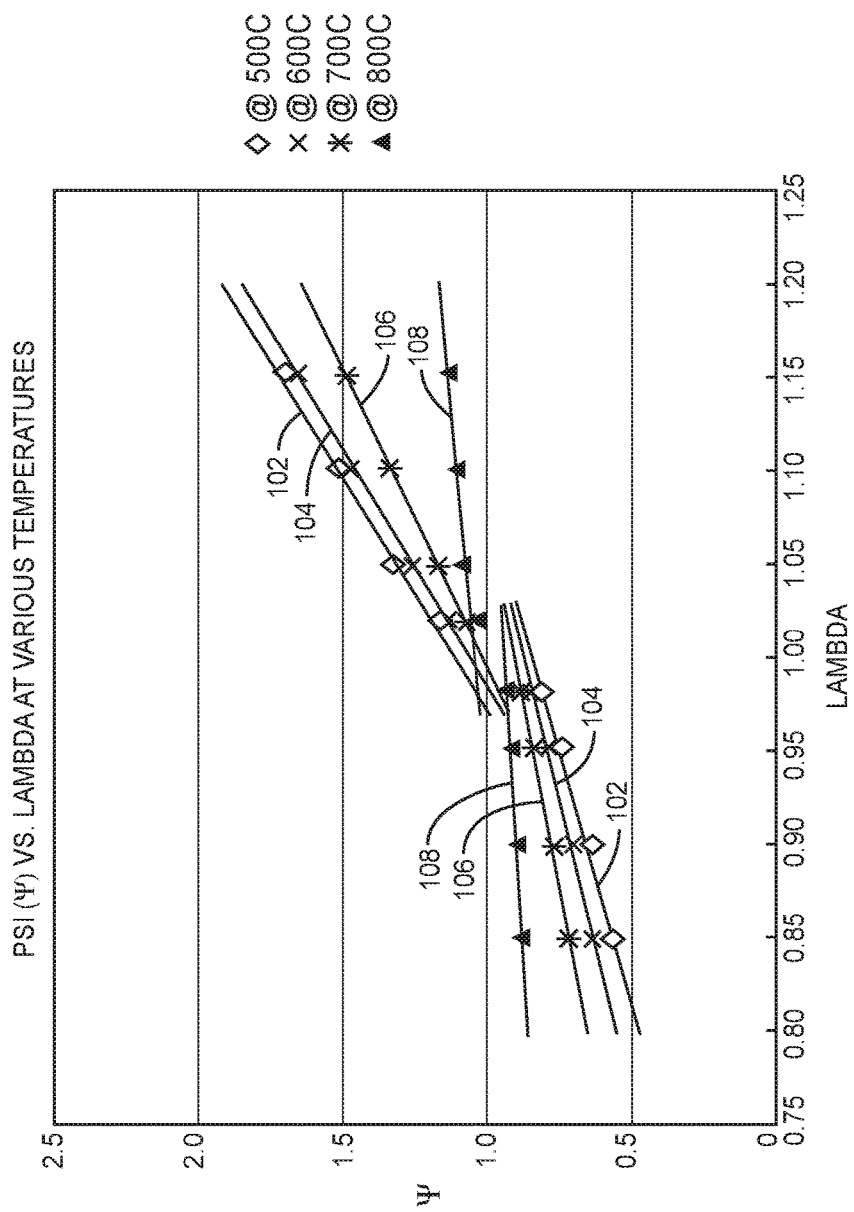
FIG. 6 shows a graph of air:fuel ratio λ versus the ratio (Ψ) of the natural logs of the current in the n-type sensing circuit and the current in the p-type sensing circuit of the apparatus of FIG. 3, at different temperatures.

In some embodiments, the air:fuel ratio is a function of the ratio of the natural log of $I_n$ to the natural log of $I_p$, and temperature of the oxygen sensor 50. More particularly, $\lambda = N \times (\ln(I_n)/\ln(I_p)) + C$, or $\lambda = N \times \Psi + C$, where $\Psi$ is the ratio of the natural logs of the currents (i.e., $\Psi = \ln(I_n)/\ln(I_p)$). As shown in FIG. 6, N and C are different for each temperature and each side of stoichiometry. For example, curve 102 shows $\Psi$ at 500° C., curve 104 shows $\Psi$ at 600° C., curve 106 shows $\Psi$ at 700° C., and curve 108 shows $\Psi$ at 800° C. Note that near stoichiometry, the accuracy becomes less reliable; but this is typically not a significant issue because the maximum power air:fuel ratio point and the maximum fuel efficiency air:fuel ratio point for most applications are well away from stoichiometry. Note also, that discrimination is better at lower temperatures. The values of N and C for various temperatures and each side of stoichiometry may be established in a calibration process, and the relevant relationships/values, perhaps represented by a table of values, stored in memory of the engine management system 30 for use by the controller 32. Thus, the controller 32 is able to determine the air:fuel ratio based on the current $I_n$ flowing through the n-type sensing circuit 92, the current $I_p$ flowing through the p-type sensing circuit 94, and the temperature of the oxygen sensor 50.

Figure 7:
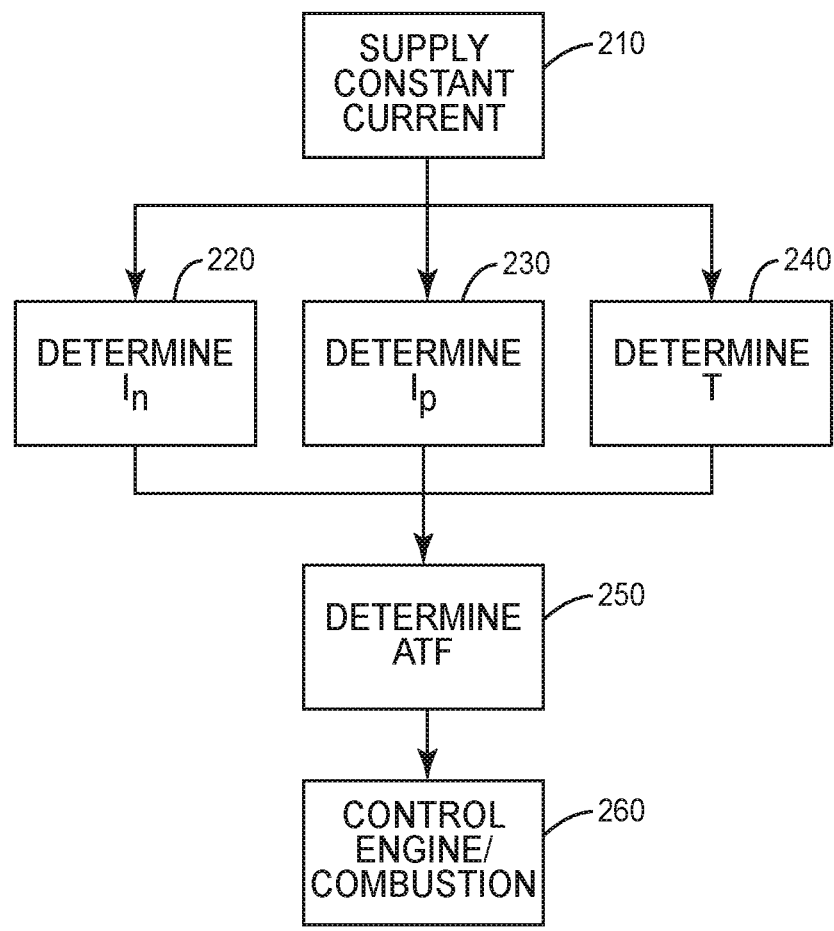
FIG. 7 shows a flowchart of an exemplary process for determining an air:fuel ratio.

The controller 32 receives the inputs derived from the oxygen sensor 50 and other sensors, and advantageously controls the operation of the fuel metering, ignition timing, and other engine functions. Relevant to the present discussion and with reference to FIGS. 5-7, the controller 32 receives voltage drop $V_2$ on line $L_{V2}$, voltage drop $V_{HS}$ on line $L_{VHS}$, voltage level $V_S$ on line $L_{VS}$, and voltage drop $V_4$ on line $L_{V4}$. The determination process typically includes, as shown in FIG. 7, supplying a constant current to the oxygen sensing portion 60 (step 210). Then, based on the inputs derived from the oxygen sensor 50 and/or the connecting circuit 90, the controller 32 determines the current $I_n$ in the n-type sensing circuit 92 (step 220), as described above. The controller 32 also determines the current $I_p$ in the p-type sensing circuit 94 (step 230), as described above. The controller 32 also determines the temperature value T representative of the temperature of the oxygen sensor 50 (step 240). Then, the controller 32 determines a first value ATF representative of the air:fuel ratio based on $I_n$, $I_p$, and T (step 250), as described above. As can be appreciated, the first value ATF is typically a $\lambda$ value. The determination of ATF may utilize a look-up table of current values, temperature values, and corresponding ATF values (e.g., $\lambda$ values), for the particular oxygen sensor 50, or the "class" of oxygen sensor 50 (e.g., particular model or series). Alternatively, AFT may be determined based on a formula, where all of $I_n$, $I_p$, an T are independent variables of the formula. Once ATF is determined, the controller 32 may then control the engine 10 based on ATF, in any suitable fashion (step 260). For example, the controller 32 may cause the fuel metering rate to be increased (lowering $\lambda$) or decreased (raising $\lambda$), via suitable control signals sent to throttle body and fuel injector 16. As can be appreciated, the controller 32 may repeat the process above to update ATF. This updating may occur periodically, or may be a triggered update (such as in response to a change in input air conditions), as is appropriate.

The discussion above has generally been in the context of the temperature of the oxygen sensor 50 being derived from the resistance of the heating portion 54 that is part of the oxygen sensor 50. Thus, the heating portion 54 fills two roles: heating the oxygen sensor 50 and sensing temperature thereof. However, in some embodiments, a temperature sensor distinct from the heating portion 54 may alternatively employed. Thus, the oxygen sensor 50 may include a thermocouple or other suitable temperature sensing device 51, in addition to the oxygen sensing portion 60 and the optional heating portion 54. Such a temperature sensor 51 is shown in FIG. 5 in dashed lines to indicate its optional presence, with its connection line to controller 32 not shown for simplicity. Note also that the temperature value need not be a calculated temperature per se, but may alternatively be any value indicative of the temperature, such as the resistance $R_H$ itself of the heater portion 54 or the resistance/voltage of temperature sensing device 51; both T and $R_H$ (and other similar values indicative of the sensed temperature) are encompassed by the term "temperature value representative of the temperature of the oxygen sensor."

Figure 8:
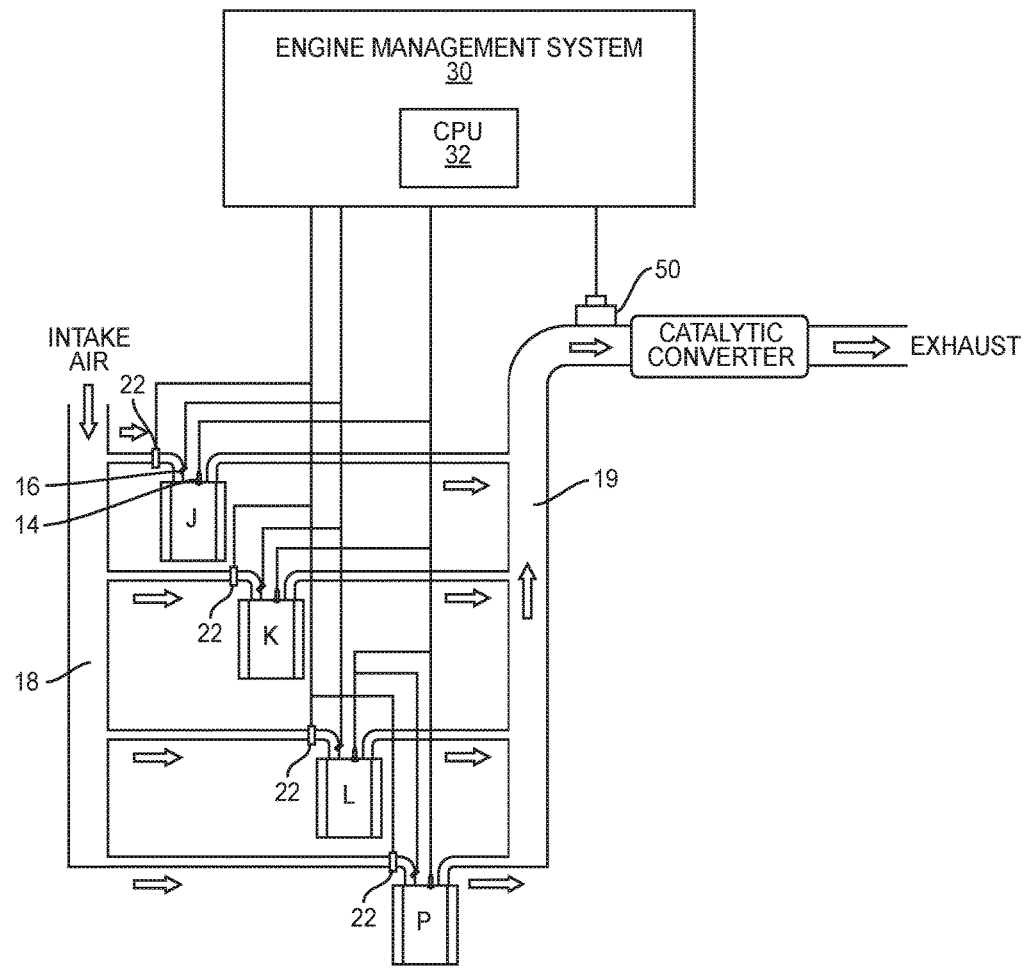
FIG. 8 shows one multiple-cylinder configuration with a common oxygen sensor for all cylinders.
Figure 9:
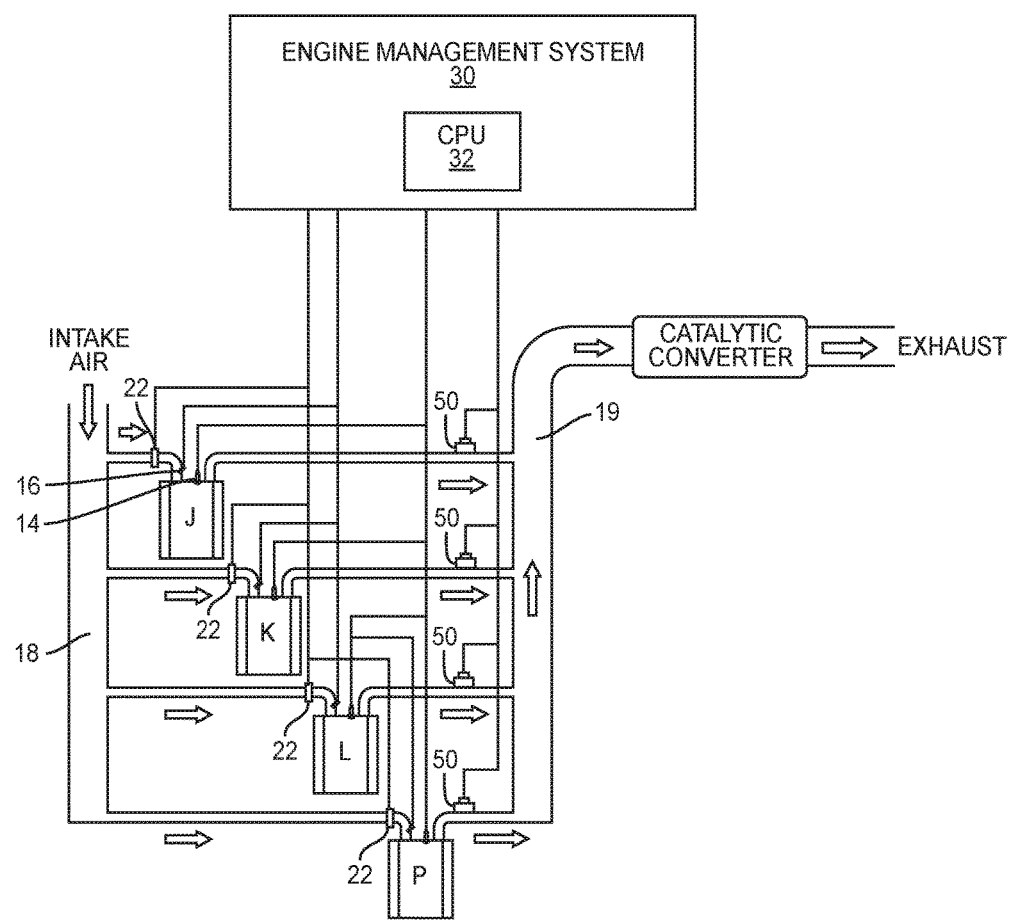
FIG. 9 shows another multiple-cylinder configuration with individual oxygen sensors for each cylinder.

The discussion above has generally been in the context of controlling an engine 10 having a single cylinder/combustion chamber. However, a similar approach may be used with engines having multiple cylinders, such as that shown in FIG. 8 with cylinders J, K, L, and P. In FIG. 8, a single common oxygen sensor 50 is used for multiple cylinders. The controller 32 may control the engine parameters (e.g., fuel metering rate) based on readings from the oxygen sensor 50, or, if the oxygen sensor 50 and controller 32 have fast enough response time, the controller 32 may be able to control the engine parameters on an individual cylinder basis. Another multi-cylinder arrangement is shown in FIG. 9, where each cylinder has its own dedicated oxygen sensor 50. With this arrangement, the controller 32 may more easily control the cylinder-specific engine parameters (e.g., fuel metering rate) on an individual cylinder basis based on readings from the corresponding oxygen sensor 50.

The discussion above has generally been in the context of the oxygen sensor 50 working in what may be referred to as a "wideband" mode, such that the oxygen sensor 50 is able to help determine oxygen levels in both the rich region and the lean region. In some embodiments, the oxygen sensor 50 may also temporarily operate as an n-type narrow-band sensor by, for example, disabling the p-type sensing circuit 94, and rely on data from the n-type sensing circuit 92 to sense when λ reaches 1.00 by the sudden step-type rise in resistance as A is increased. Or, alternatively, the oxygen sensor 50 may also temporarily operate as a p-type narrow-band sensor by, for example, disabling the n-type sensing circuit 92, and rely on data from the p-type sensing circuit 94 to sense when λ reaches 1.00 by the sudden step-type rise in resistance as λ is decreased.

The discussion above has generally been in the context of an internal combustion engine; however, the present invention is not limited in application to internal combustion engines. Indeed, the oxygen sensing method described above can be used to control combustion processes generally. Thus, for example, the method(s) described herein may be used in combustion processes in a furnace or a water heater. As with the engine-based discussion above, the oxygen sensor 50 is disposed so as to sense exhaust gases in the exhaust plenum 19 from the combustion process.

The methods and engine control systems discussed above provide the opportunity for enhanced combustion and/or engine control so that greater fuel economy and/or reduced emissions may be achieved.

As used herein, an air:fuel ratio may be expressed as an un-normalized ratio (e.g., 14.7:1 for gasoline), or as a normalized ratio (e.g., λ).

The disclosure of all patents and patent publications mentioned above are incorporated herein by reference in their entirety.

The present invention may, of course, be carried out in other specific ways than those herein set forth without departing from the scope of the invention. The present embodiments are, therefore, to be considered as illustrative and not restrictive.

What is claimed is:

1. A wideband oxygen sensor, comprising:
a substrate, the substrate being dielectric;
a first common electrode affixed to the substrate and having first and second combs disposed on respective first and second lateral sides of the first common electrode, each having a plurality of fingers;
a first sensing electrode affixed to the substrate and disposed on the first lateral side of the first common electrode in spaced relation thereto;
a second sensing electrode affixed to the substrate and disposed on the second lateral side of the first common electrode in spaced relation thereto;
a first semiconductor bridge, comprising an n-type semiconducting material, disposed so as to interconnect the first comb and the first sensing electrode, wherein the first semiconductor bridge is attached directly to the first common electrode;
a second semiconductor bridge, comprising a p-type semiconducting material, disposed in spaced relation to the n-type semiconducting material and disposed so as to interconnect the second comb and the second sensing electrode; wherein the second semiconductor bridge is attached directly to the first common electrode and not in physical contact with the first semiconductor bridge;
wherein the first and second semiconductor bridges are separated from each other by a lateral gap.

2. The wideband oxygen sensor of claim 1, further comprising:
a first porous dielectric protective layer covering the n-type semiconducting material;
a second porous dielectric protective layer covering the p-type semiconducting material.

3. The wideband oxygen sensor of claim 2, wherein the first porous dielectric layer comprises one or more catalytic precious metals and cerium oxide.

4. The wideband oxygen sensor of claim 1, further comprising a heater portion affixed to the substrate in spaced relation to the first common electrode and electrically insulated from the n-type semiconducting material and the p-type semiconducting material.

5. The wideband oxygen sensor of claim 4:
wherein the first common electrode comprises a first terminal;
wherein the first sensing electrode comprises a second terminal;
wherein the second sensing electrode comprises a third terminal;
wherein the heater portion comprises a fourth terminal.

6. The wideband oxygen sensor of claim 5, wherein first terminal is operatively connected to the heater portion.

7. The wideband oxygen sensor of claim 4:
wherein the dielectric substrate has first and second oppositely facing surfaces;
wherein the heater portion is disposed on the first surface of the substrate;
wherein the first common electrode and both the first and second sensing electrodes are disposed closer to the second surface of the substrate than to the heater portion.

8. The wideband oxygen sensor of claim 4, wherein the heater portion comprises platinum.

9. The wideband oxygen sensor of claim 4:
wherein the first common electrode is disposed on the substrate;
wherein the first sensing electrode is disposed on the substrate;
wherein the second sensing electrode is disposed on the substrate;
wherein the heater portion is affixed to the substrate in spaced relation to the electrodes.

10. A wideband oxygen sensor, comprising:
a substrate, the substrate being dielectric;
a first common electrode affixed to the substrate;
an n-type oxygen sensing portion comprising an n-type semiconductor layer;
a p-type oxygen sensing portion comprising an p-type semiconductor layer;
wherein the n-type sensing portion and the p-type sensing portion share the first common electrode;
wherein the n-type semiconductor layer and the p-type semiconductor layer attach directly to the first common electrode, but are not in physical contact with each other such that a lateral gap exists between the n-type semiconductor layer and the p-type semiconductor layer.

11. The wideband oxygen sensor of claim 10, further comprising:
a first porous dielectric protective layer covering the n-type semiconducting material;
a second porous dielectric protective layer covering the p-type semiconducting material.

12. The wideband oxygen sensor of claim 10, further comprising a heater portion affixed to the substrate in spaced relation to the first common electrode and electrically insulated from the n-type oxygen sensing portion and the p-type oxygen sensing portion.

13. The wideband oxygen sensor of claim 12:
wherein the dielectric substrate has first and second oppositely facing surfaces;
wherein the heater portion is disposed on the first surface of the substrate;
wherein the first common electrode and both the n-type oxygen sensing portion and the p-type oxygen sensing portion are disposed closer to the second surface of the substrate than to the heater portion.

14. The wideband oxygen sensor of claim 12, wherein the heater portion comprises platinum.

15. A sensor system, comprising:
a wideband oxygen sensor, the wideband oxygen sensor comprising:
a substrate, the substrate being dielectric;
a first common electrode affixed to the substrate;
an n-type oxygen sensing portion comprising an n-type semiconductor layer;
a p-type oxygen sensing portion comprising an p-type semiconductor layer;
wherein the n-type sensing portion and the p-type sensing portion share the first common electrode;
wherein the n-type semiconductor layer and the p-type semiconductor layer attach directly to the first common electrode, but are not in physical contact with each other such that a lateral gap exists between the n-type semiconductor layer and the p-type semiconductor layer;
connecting circuits operatively connected to the first common electrode, the n-type semiconductor layer, and the p-type semiconductor layer, the connecting circuits comprising:
a constant current source;
a first pair of resistors connected in series between the n-type semiconductor layer and the constant current source;
a second pair of resistors connected in series between the p-type semiconductor layer and the constant current source;
an n-type sensing circuit and a p-type sensing circuit;
wherein the n-type sensing circuit comprises the n-type sensing portion, the constant current source, and the first pair of resistors;
wherein the p-type sensing circuit comprises the p-type sensing portion, the constant current source, and the second pair of resistors.

* * * * *